(12) United States Patent
Ni et al.

(10) Patent No.: US 6,294,164 B1
(45) Date of Patent: *Sep. 25, 2001

(54) NATURAL KILLER CELL ENHANCING FACTOR C

(75) Inventors: Jiar Ni, Gaithersburg; Guo-Liang Yu, Darnestown; Reiner Gentz, Silver Spring; Craig A. Rosen, Laytonsville, all of MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/407,891

(22) Filed: Sep. 29, 1999

Related U.S. Application Data

(62) Division of application No. 08/467,265, filed on Jun. 6, 1995.

(51) Int. Cl.[7] .......................... A61K 38/19; C07K 14/52; C12N 5/10; C12N 15/19; C12N 15/64
(52) U.S. Cl. .......................... 424/85.1; 530/351; 514/2; 514/8; 514/12; 514/885; 536/23.1; 536/23.5; 435/69.5; 435/71.2; 435/252.3; 435/254.11; 435/325; 435/471; 435/320.1
(58) Field of Search .......................... 530/351; 435/69.5, 435/71.1, 71.2, 325, 471, 252.3, 254.11, 320.1; 514/2, 8, 12, 885; 424/85.1; 536/23.1, 23.5

(56) References Cited

U.S. PATENT DOCUMENTS

| 5,185,431 | 2/1993 | Yoshimatsu et al. ................. 530/351 |
| 5,250,295 | 10/1993 | Shau et al. .......................... 424/85.2 |
| 5,316,933 | 5/1994 | Yoshimatsu et al. ............. 435/240.1 |
| 5,610,286 | 3/1997 | Shau et al. .......................... 536/23.5 |

FOREIGN PATENT DOCUMENTS

| WO 93/08827 | 5/1993 | (WO) . |
| WO 96/39424 | 12/1996 | (WO) . |

OTHER PUBLICATIONS

Mikayama et al. Proc. Natl. Acad. Sci. USA vol.90, pp. 10056–10060, 1993.*
Voet et al. Biochemistry. John Wiley & Sons, Inc. pp. 126–128 and 228–234, 1990.*
Genbank Accession No. G01790 (Dec. 21, 1999).
Genbank Accession No. H89943 (Nov. 28, 1995).
Genbank Accession No. H90488 (Nov. 28, 1995).
Genbank Accession No. U25182 (May 9, 1995).
Geneseq Accession No. T20740 (Jul. 26, 1996).
Genbank Accession No. R27341 (Apr. 24, 1995).
Genbank Accession No. F00772 (Mar. 14, 1995).
Genbank Accession No. R27342 (Apr. 24, 1995).
George et al. "Macromolecular Sequencing and Synthesis: Selected Methods and Applications"; Alan R. Liss, Inc., Ch. 12, pp. 127–149 (1988).
Chae et al. (1994) PNAS USA 91:7017–7021.

* cited by examiner

Primary Examiner—Prema Mertz
(74) Attorney, Agent, or Firm—Human Genome Sciences, Inc.

(57) ABSTRACT

A human natural killer cell enhancing factor C and DNA (RNA) encoding such polypeptide and a procedure for producing such polypeptide by recombinant techniques is disclosed. Also disclosed are methods for utilizing such polypeptide for preventing and/or treating viral infections, inflammation, neoplasia and damage from superoxide radicals. Diagnostic assays for identifying mutations in nucleic acid sequence encoding a polypeptide of the present invention and for detecting altered levels of the polypeptide of the present invention for detecting diseases, for example, cancer, are also disclosed.

38 Claims, 8 Drawing Sheets

```
                10                  30                  50
    AAGGGAACGTGTTTCTCCCCTCGTTTGGTCATGGAGGCGCTGCCCCTGCTAGCCGCGACA
                                    M  E  A  L  P  L  L  A  A  T
          70                  90                 110
    ACTCCGGACCACGGCCGCCACCGAAGGCTGCTTCTGCTGCCGCTACTGCTGTTCCTGCTG
     T  P  D  H  G  R  H  R  R  L  L  L  L  P  L  L  L  F  L  L
             130                 150                 170
    CCGGCTGGAGCTGTGCAGGGCTGGGAGACAGAGGAGAGGCCCCGGACTCGCAAGAGGAG
     P  A  G  A  V  Q  G  W  E  T  E  E  R  P  R  T  R  E  E  E
             190                 210  ,              230
    TGCCACTTCTACGCGGGTGGACAAGTGTACCCGGGAGAGGCATCCCGGGTATCGGTCGCC
     C  H  F  Y  A  G  G  Q  V  Y  P  G  E  A  S  R  V  S  V  A
             250                 270                 290
    GACCACTCCCTGCACCTAAGCAAAGCGAAGATTTCCAAGCCAGCGCCCTACTGGGAAGGA
     D  H  S  L  H  L  S  K  A  K  I  S  K  P  A  P  Y  W  E  G
             310                 330                 350
    ACAGCTGTGATCGATGGAGAATTTAAGGAGCTGAAGTTAACTGATTATCGTGGGAAATAC
     T  A  V  I  D  G  E  F  K  E  L  K  L  T  D  Y  R  G  K  Y
             370                 390                 410
    TTGGTTTTCTTCTTCTACCCACTTGATTTCACATTTGTGTGTCCAACTGAAATTATCGCT
     L  V  F  F  F  Y  P  L  D  F  T  F  V  C  P  T  E  I  I  A
             430                 450                 470
    TTTGGCGACAGACTTGAAGAATTCAGATCTATAAATACTGAAGTGGTAGCATGCTCTGTT
     F  G  D  R  L  E  E  F  R  S  I  N  T  E  V  V  A  C  S  V
             490                 510                 530
    GATTCACAGTTTACCCATTTGGCCTGGATTAATACCCCTCGAAGACAAGGAGGACTTGGG
     D  S  Q  F  T  H  L  A  W  I  N  T  P  R  R  Q  G  G  L  G
             550                 570                 590
    CCAATAAGGATTCCACTTCTTTCAGATTTGACCCATCAGATCTCAAAGGACTATGGTGTA
     P  I  R  I  P  L  L  S  D  L  T  H  Q  I  S  K  D  Y  G  V
             610                 630                 650
    TACCTAGAGGACTCAGGCCACACTCTTAGAGGTCTCTTCATTATTGATGACAAAGGAATC
     Y  L  E  D  S  G  H  T  L  R  G  L  F  I  I  D  D  K  G  I
             670                 690                 710
    CTAAGACAAATTACTCTGAATGATCTTCCTGTGGGTAGATCAGTGGATGAGACACTACGT
     L  R  Q  I  T  L  N  D  L  P  V  G  R  S  V  D  E  T  L  R
             730                 750                 770
    TTGGTTCAAGCATTCCAGTACACTGACAAACACGGAGAAGTCTGCCCTGCTGGCTGGAAA
     L  V  Q  A  F  Q  Y  T  D  K  H  G  E  V  C  P  A  G  W  K
             790                 810                 830
    CCTGGTAGTGAAACAATAATCCCAGATCCAGCTGGAAAGCTGAAGTATTTCGATAAACTG
     P  G  S  E  T  I  I  P  D  P  A  G  K  L  K  Y  F  D  K  L
             850                 870                 890
    AATTGAGAAATACTTCTTCAAGTTATGATGCTTGAAAGTTCTCAATAAAGTTCACGGTTT
     N
             910
    CATTACCACAAAAAAAAA
```

FIG.1

```
                                                                    Consensus #1
    M . .   .   .   .   .   .   .   .   .   .   .   .   .   .   .   Majority
    M A S G N - - - - - - - - - - - - - - - - - - - - - - - - - - -
                        10                      20                  30
 1  E A L P - - L L - A A T T P D H G R H R R L L L L P L L L - - -  NKEF C
 1  S - - - - - - - - - - - - - - - - - - - - - - - - - - - - - - -  NKEF A
 1  A A A G R L L W S S V A R H A S A I S R - - - - - - - - - - - -  NKEF B
 1  - - - - - - - - - - - - - - - - - - - - - - - - - - - - - - - -  MER5
 1  S - - - - - - - - - - - - - - - - - - - - - - - - - - - - - - -  MSP23

Consensus #1
    .   .   .   .   .   .   .   .   .   .   .   .   .   .   .   .   Majority
                        40                      50                  60
28  F L L P A G A V Q G W E T E E R P R T R E E E C H F Y A G G       NKEF C
 6  - - - - - - - - - - - - - - - - - - - - - - - - - - - - -       NKEF A
 6  - - - - - - - - - - - - - - - - - - - - - - - - - - - - -       NKEF B
23  - S I S A S T V L - - - - - R P V A S R R T C - - - L T D       MER5
 6  - - - - - - - - - - - - - - - - - - - - - - - - - - - - -       MSP23

Consensus #1
    .   .   .   .   .   .   .   .   . A P .   .   . A K I G K P A P N  Majority
                        70                      80                  90
58  Q V Y P G E A S R V S V A D H S L H L S K A · · · S · · · · · Y    NKEF C
 6  - - - - - - - - - - - - - - - - - - - - - - - - H - - - - - -     NKEF A
 6  - - - - - - - - - - - - - - - - - - - - - A R - - - - - - - D     NKEF B
43  I L W S A S A Q G K S A F S T S S S F H T - - - P A V T Q H - Y    MER5
 6  - - - - - - - - - - - - - - - - - - - - - A K - - C Y - - - -     MSP23
```

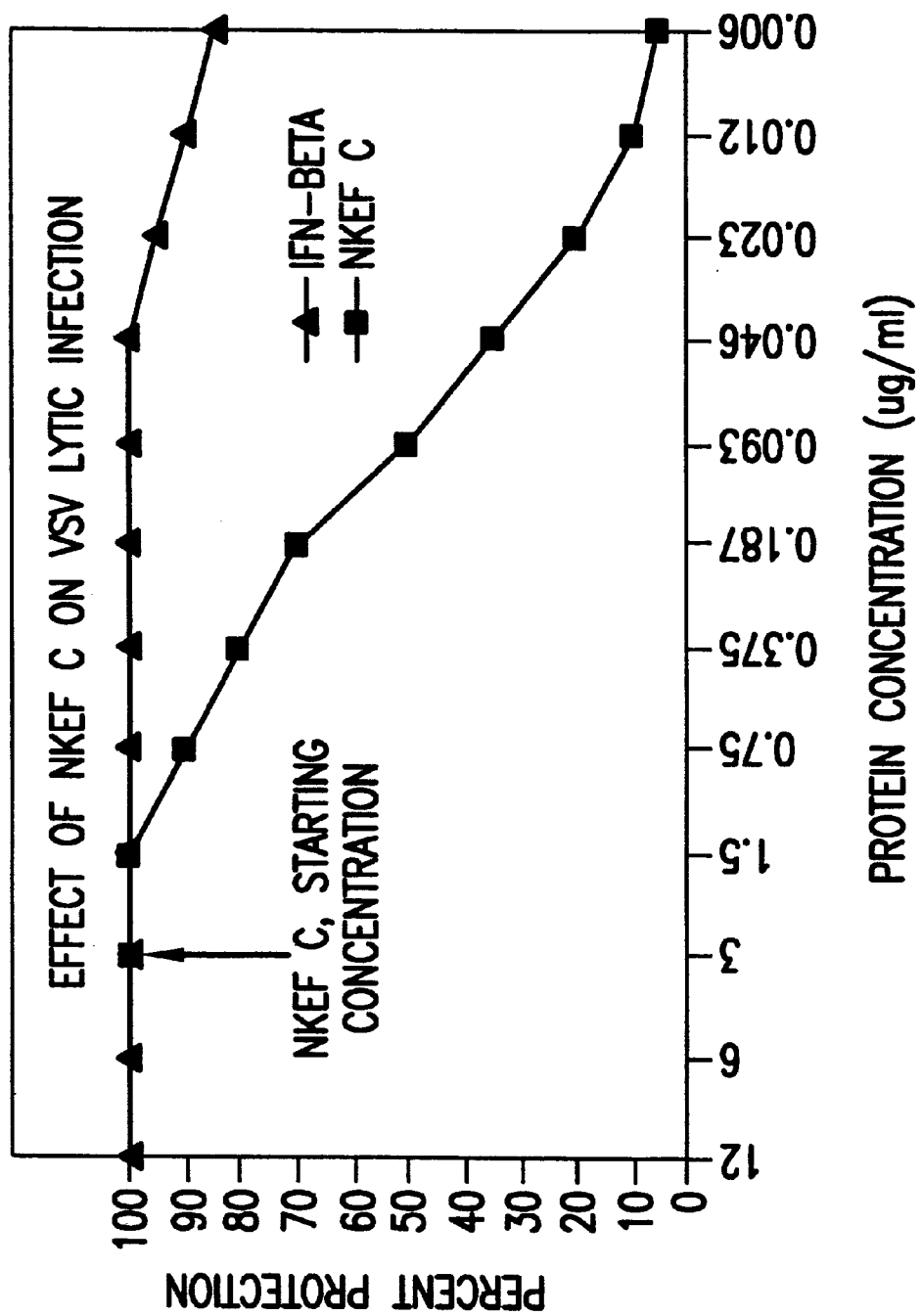

NATURAL KILLER CELL ENHANCING FACTOR C

This application is a divisional of U.S. application Ser. No. 08/467,265 filed Jun. 6, 1995, which claims benefit under 35 U.S.C. §120, and is hereby incorporated by reference in its entirety.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as a natural killer cell enhancing factor C, sometimes hereinafter referred to as "NKEF C." The invention also relates to inhibiting the action of such polypeptides.

Natural killer (NK) cells are a subset of lymphocytes capable of lysing a variety of tumor cells without prior activation. Lymphokine-activated killer (LAK) cells are mainly NK cells activated by interleukin-2, and are capable of lysing wider ranges of tumor cells with higher cytotoxic activity. NK cells are proposed to function as natural surveillance to deter cancer development in the body (Whiteside, T. and Herberman, R. B., *Clin. Immunol. Immunopathol.*, 58:1–23 (1989) and Trinchieri, G., *Adv. Immunol.*, 47:187–376 (1989)). LAK cells, in combination with IL-2, have been used in experimental models and in clinical studies to successfully treat some metastatic tumors (Rosenberg, S. A., et al., *N. Engl. J. Med.*, 316:889–897 (1987)). NK cells are also important controlling viral infection and the regulation of hematopoiesis (Trinchieri (1989), Kiessling, R., et al., *Eur. J. Immunol.*, 7:655–663 (1977), Kiessling, R. and Wigzell, H., *Curr. Top. Microbiol. Immunol.*, 92:107–123 (1981)). Given the important roles of NK/LAK cells in maintaining the host well-being, it is not surprising that their activities are stringently controlled in vivo.

NK/LAK activity is influenced by various cellular and humoral components in the blood (Golub, S. H., et al., R. E. Schmidt (ed.): *Natural Killer Cells: Biology and Clinical Application*, pp. 203–207, S. Karger, A G Basel (1990)), for instance, the regulation by red blood cells (RBC), which enhance NK cytotoxicity against different target cells (Shau, H., et al., E. Lotzova (ed.): *Natural Killer Cells: Their Definition, Functions, Lineage and Regulation*: pp. 235–349, S. Karger, A G Basel (1993)) and which also upregulate LAK development (Yannelli, J. R., et al., *Cancer Res.*, 48:5696–5700 (1988)).

Oxidative stress is an important yet incompletely understood phenomenon, cells use reactive oxygen species (ROS) to carry out essential functions. Under proper control, ROS initiates conception, cell differentiation and proliferation. If not properly controlled, ROS causes serious damage to cellular components which may lead to apoptotic cell death. ROS are known to cause large-scale cell death, senile changes, inflammation and tissue injuries in the body.

Two NKEF genes (NKEF-A and B) from a K562 erythroleukemia cell cDNA library have recently been cloned (Shau, H., et al., *Immunogenetics*, 40:129–134 (1994)). They have been identified as members of a new class of highly conserved antioxidant proteins. They share extensive homology with each other (88% identical at the amino acid level, 71% identical in nucleotide sequence). It is not clear whether the dimeric NKEF is a homo- or hetero-dimer of the A or B peptides in vivo. NKEF A and NKEF B are differentially expressed in different tissues. NKEF A and NKEF B have similar antioxidant activity, but NKEF A has higher NK enhancing activity than NKEFB. Transfecting NKEF DNA into different cells resulted in cell-type-dependent enhanced cell proliferation or growth inhibition.

This large family of proposed antioxidant genes are highly conserved from bacteria to mammals while mammals have been found to carry more than one NKEF-related gene, bacteria and yeast have been found to carry only one copy (Sauri, H., et al.). Members of this family have been described as thiol-specific antioxidants. These genes (NKEF-A and B) encode recombinant proteins which possess antioxidant function in the protection of protein and DNA from oxidative damage. NKEF is a 44 kD protein isolated from red blood cell cytosol that increases NK cell cytotoxicity to tumor target cells (Shau, H., et al., *Cell. Immunol.*, 147, 1–11 (1993)). NKEF is a diner protein composed of two approximately 22 kD monomers linked by disulphide bonds.

Two of the other NKEF-related proteins are human thiol-specific antioxidant protein (HPRP) isolated from a hippocampus cDNA library, and the proliferation-associated gene (PAG), found to be hyperexpressed in transformed cells. HPRP is 95% identical to NKEF B by nucleotide sequences, and 93% identical by amino acid sequence. Alignment with NKEF-related proteins in other species suggested that NKEF B and HPRP are the same. PAG shares 98% identity with NKEF A by nucleotide sequence, and 97% at the amino acid level, and may be identical to NKEFA.

In mice, the two homologous genes are MSP23 and MER5. MER5 is 61% identical to NKEF A in amino acid sequence and 64% identical to NKEFB. Even more striking is MSP23, which is 93% identical to NKEF A and 76% identical to NKEFB. MSP23 is induced by oxidative stress in mouse macrophage. MER5 is hyperexpressed in murine erythroleukemic cells, and is necessary for differentiation in those cells. NKEF and NKEF-related proteins show no sequence homology to other known antioxidants, such as catalase, superoxide dismutase, or glutathione peroxidase, nor do they exhibit the enzymatic activity of those antioxidants.

This family of antioxidant genes has been found to selectively suppress activation of NF-κB. Nuclear factor κB (NF-κB) is a transcriptional activator important for the expression of human immunodeficiency virus type I (HIV-I) upon T-cell activating stimuli (Englund, G. et al., *Virology*, 181:150–157 (1991), Nabel, G., and Baltimore, D., *Nature* (London), 326:711–713 (1987)). Most of the target genes of NF-κB in T-cells and other types encode proteins involved in immune, inflammatory and acute phase responses.

The polypeptide of the present invention has been putatively identified as a natural killer enhancing factor C due to its amino acid sequence homology with human natural killer enhancing factor. This identification has been made as a result of amino acid sequence homology.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to inhibit the growth of leukemia cells, to treat viral infection, to augment the effects of natural killer protein to treat neoplasias such as tumors and cancers, to prevent inflammation, and to prevent damage from superoxide radicals in the body, for example, tissue injury and aging.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with another aspect of the present invention, there are provided NKEF C agonist compounds which mimic NKEF C and bind to NKEF C receptors to elicit the biological functions of wild-type NKEF C.

In accordance with yet another aspect of the present invention, there are provided antagonists to such polypeptides, which may be used to inhibit the action of such polypeptides, for example, in the treatment of bone marrow transplant rejection.

In accordance with still another aspect of the present invention, there are provided diagnostic assays for detecting diseases related to the expression of the polypeptides and for detecting mutations in the nucleic acid sequences encoding such polypeptides.

In accordance with yet another aspect of the present invention, there is provided a process for utilizing such polypeptides, or polynucleotides encoding such polypeptides, as research reagents for in vitro purposes related to scientific research, synthesis of DNA and manufacture of DNA vectors, for the purpose of developing therapeutics and diagnostics for the treatment of human disease.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 depicts the cDNA and corresponding deduced amino acid sequence of the polypeptide of the present m invention. The standard one-letter abbreviations for amino acids are used. Sequencing was performed using a 373 automated DNA sequencer (Applied Biosystems, Inc.).

Figure 2B:
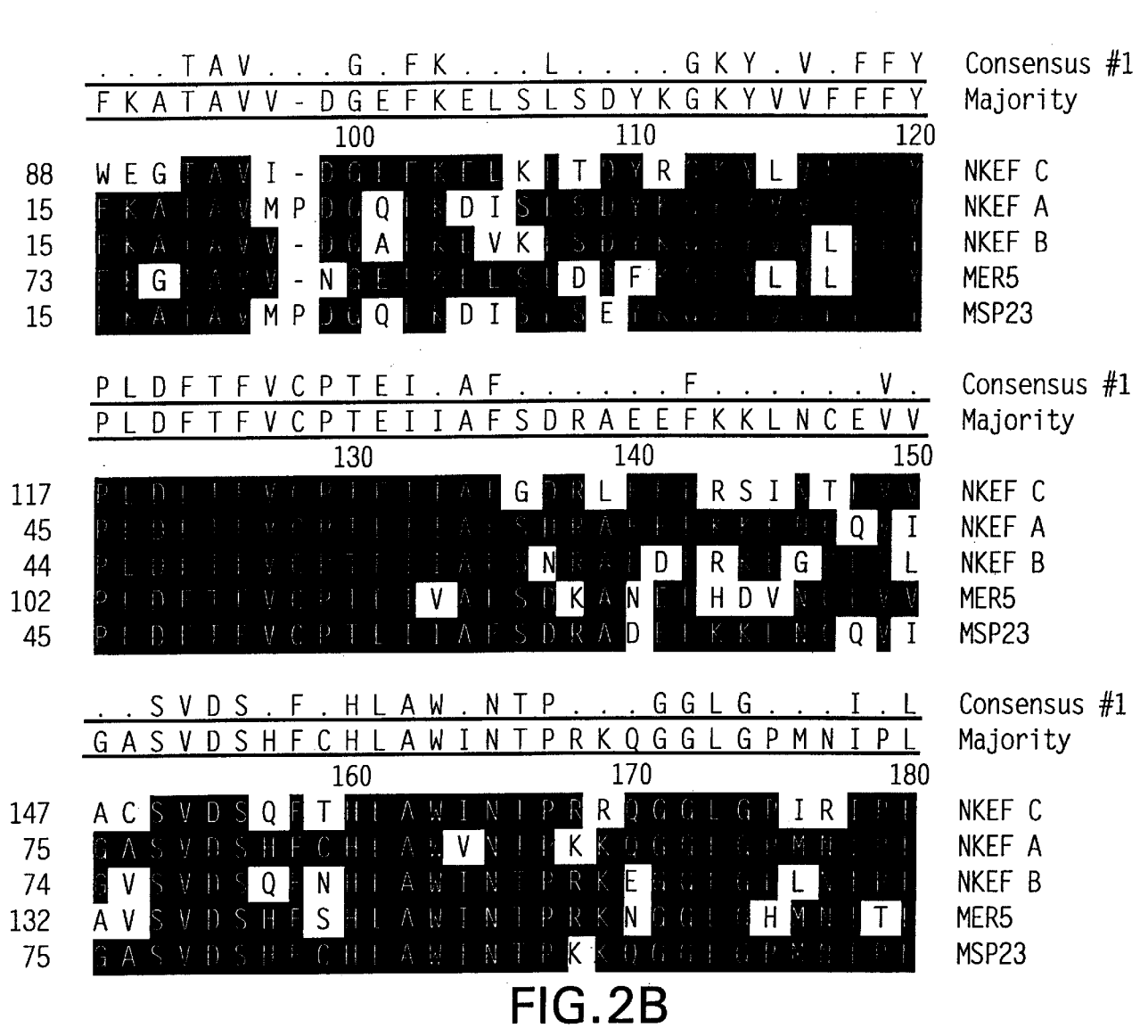
Figure 2C:
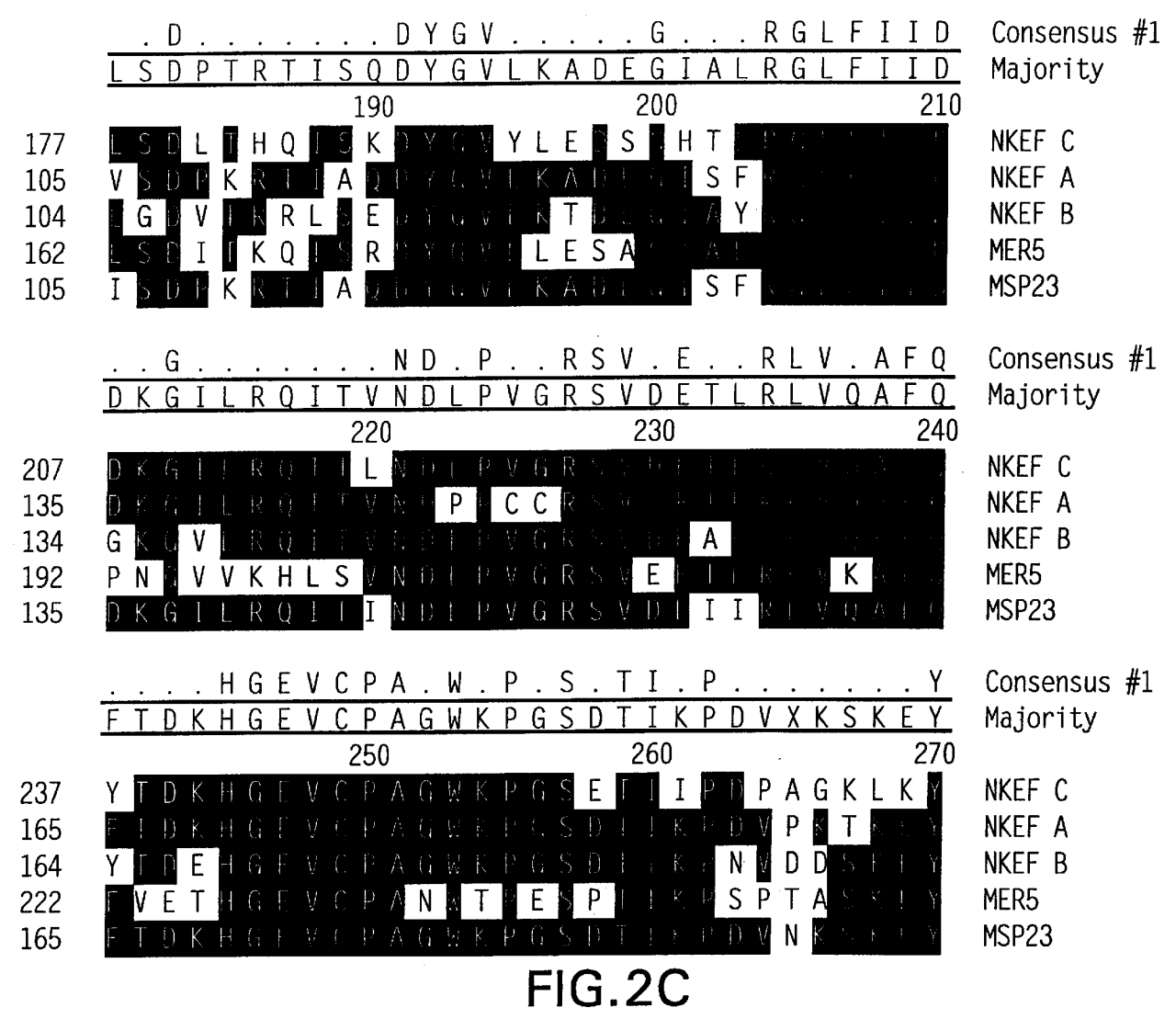

FIGS. 2A–2D show the amino acid sequence homology between the polypeptide of the present invention (top comparative line of each row, from SEQ ID NO:2), human NKEF A (second comparative line of each row, SEQ ID NO: 14), NKEF B (third comparative line of each row, SEQ ID NO:15), MER5 (fourth comparative line of each row, SEQ ID NO:16) and MSP23 (fifth comparative line of each row, SEQ ID NO: 17).

FIG. 5 illustrates the effect of NKEF C on VSV lytic infection.

Figure 3:
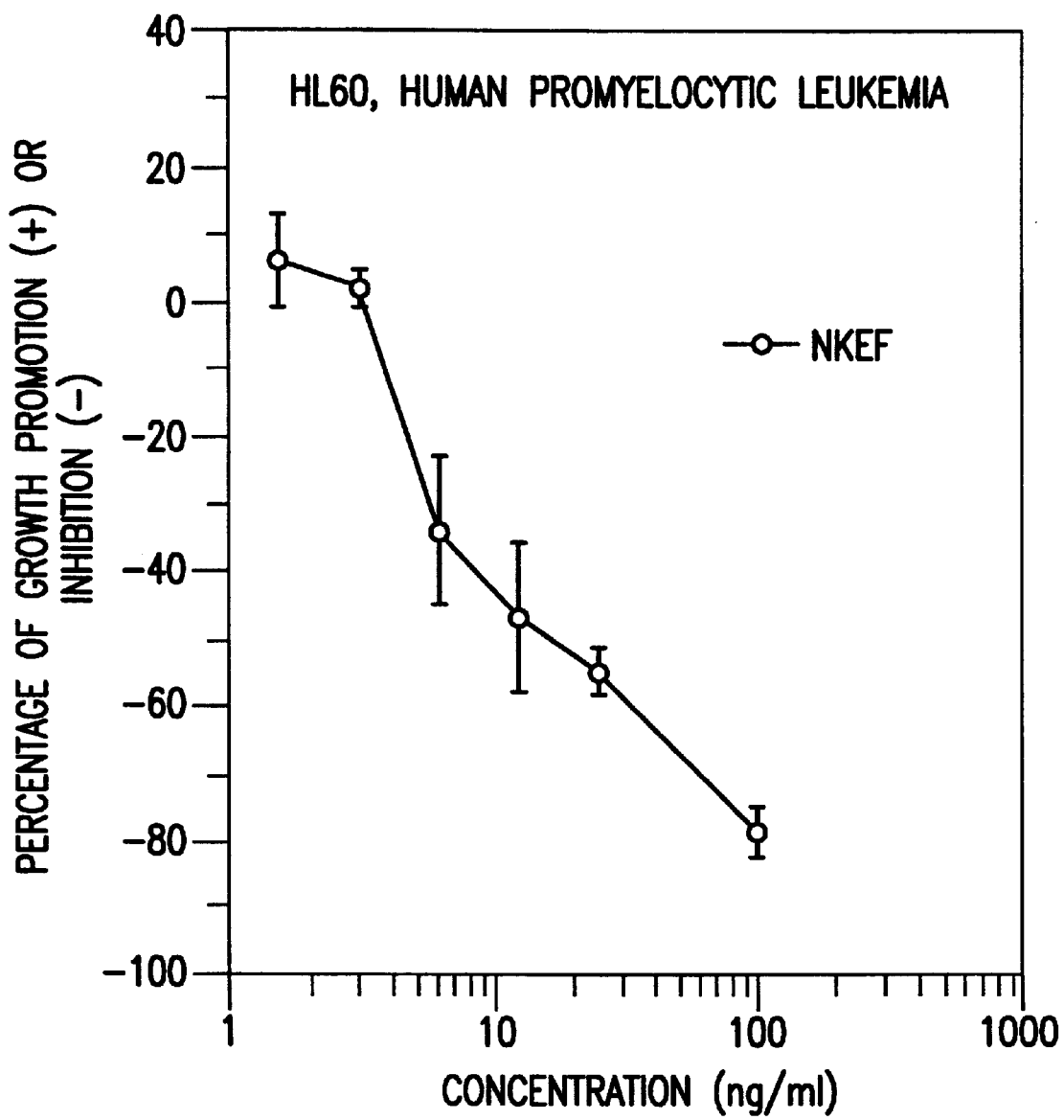
FIG. 3 illustrates the growth inhibitory activity of NKEF C against HL60 human promyelocytic leukemia cells.
Figure 4:
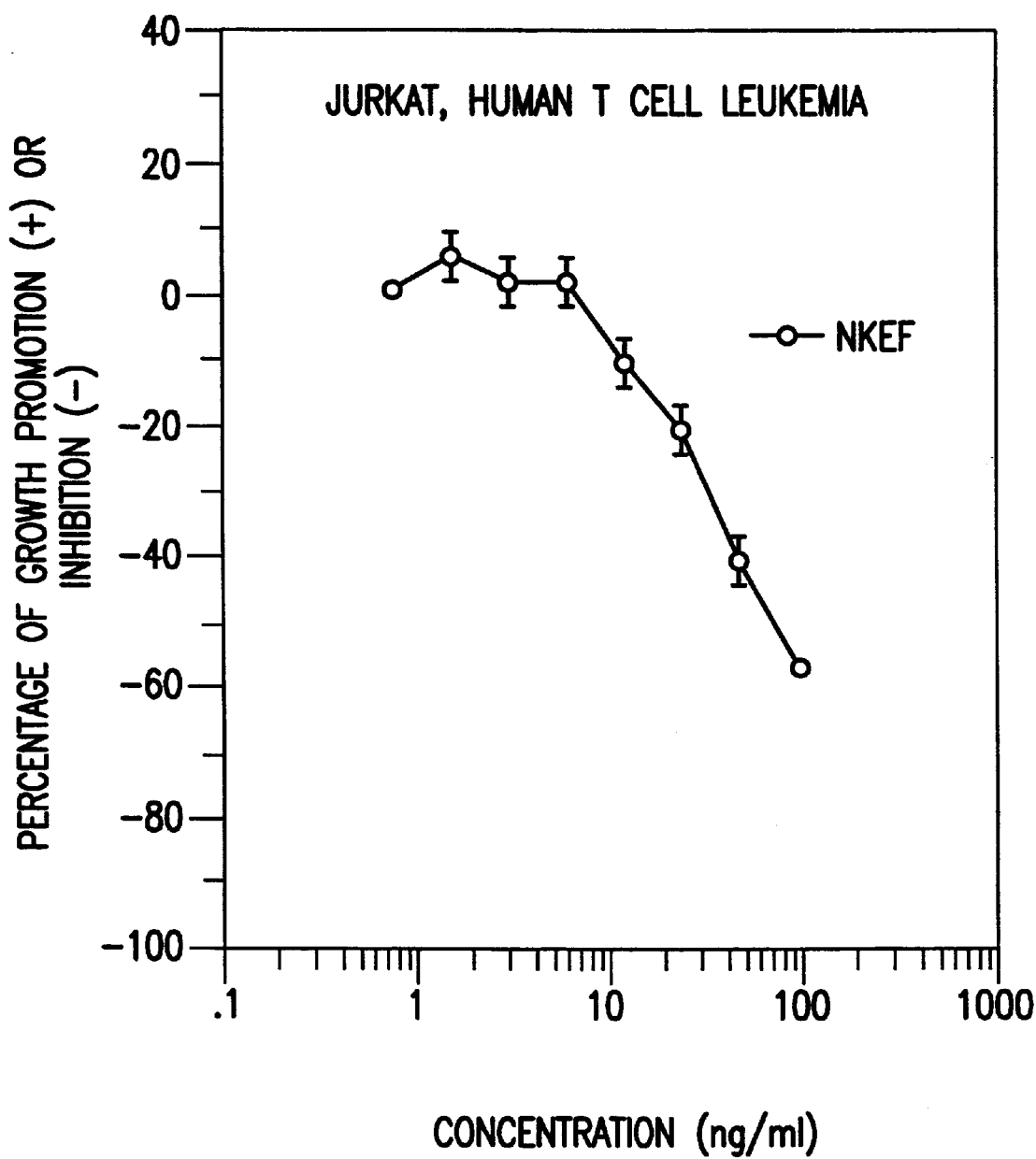
FIG. 4 illustrates the growth inhibitory activity of NKEF C against Jurkat human T-cell leukemia cells.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 97157 on May 22, 1995 at the American Type Culture Collection, ATCC, 10801 University Boulevard, Manassas, Va. 20110-2209.

The polynucleotide of the present invention is highly expressed in heart, liver, skeletal muscle, pancrease, testis, and ovary, moderately expressed in placenta, lung, prostate, small intestine and colon, and lowly expressed in brain, spleen, thymus and peripheral blood leukocite. The polynucleotide of this invention was discovered in a cDNA library derived from cyclohexamide treated CEM cells. It is structurally related to a family of highly conserved oxidative stress genes. It contains an open reading frame encoding a protein of 271 amino acid residues of which approximately the first 30 amino acids residues are the putative leader sequence such that the mature protein comprises 241 amino acids. The protein exhibits the highest degree of homology to NKEF B expressed from NK-sensitive erythroleukemic cell line K 562, as shown in Sauri, H., et al. with 68.182% identity and 83.333% similarity over the entire amino acid stretch. These proteins are significantly homologous to several other proteins (thIol-specific antioxidants) from a wide variety of organisms ranging from prokaryotes to mammals, especially with regard to several well-conserved motifs in the amino acid sequences.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length NKEF C gene may be used as a hybridization probe for a cDNA library to isolate the full length gene and to isolate other genes which have a high sequence similarity to the NKEF C gene or similar biological activity. Probes of this type preferably have at least 30 bases and may contain, for example, 50 or more bases. The probe may also be used to identify a cDNA clone corresponding to a full length transcript and a genomic clone or clones that contain the complete NKEF C gene including regulatory and promotor regions, exons, and introns. An example of a screen comprises isolating the coding region of the NKEF C gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, And which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit (s) referred to herein will be maintained under the texmr of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to an NKEF C polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 85% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Strentomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9

(Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The NKEF C polypeptide of the present invention has been shown to significantly augment NK cell-mediated cytotoxicity when added at the initiation of cytotoxicity assays and NKEF, accordingly, may be employed to regulate NK function.

The NKEF C polypeptide may be employed to enhance NK activity and therefore deter cancer development in the body. The NKEF C polypeptide may also be employed for immunoregulation of NK activity and may be important for cells in coping with oxidative insults which leads to tissue injury and aging, for example.

The NKEF C polypeptide of the present invention may also be employed to prevent inflammation.

The NKEF C polypeptide of the present invention may also be employed to prevent NK-κB activity and prevent viral transcription and therefore the proliferation of viral infections. Oxidative stress induces NF-κB activation in T-cells by the transactivator TAX from human T-cell leukemia type 1 (HDLV-1) and therefore induce viral transcription. Accordingly, Human immunodeficiency virus type 1 (HIV-1) and HDLV-1 may also be treated with the NKEF C polypeptide of the present invention.

The polypeptide of the present invention may also be employed to inhibit the cytopathic effect of vesicular stromatitis virus and to inhibit the growth of leukemia cells.

The polynucleotides and polypeptides of the present invention may also be employed as research reagents and materials for discovery of treatments and diagnostics to human disease.

This invention provides a method for identification of the receptor for the NKEF C polypeptide. The gene encoding the receptor can be identified by numerous methods known to those of skill in the art, for example, ligand panning and FACS sorting (Coligan, et al., Current Protocols in Imm., 1(2), Chapter 5, (1991)). Preferably, expression cloning is employed wherein polyadenylated RNA is prepared from a cell responsive to the NKEF C polypeptide, and a cDNA library created from this RNA is divided into pools and used to transfect COS cells or other cells that are not responsive to the NKEF C polypeptide. Transfected cells which are grown on glass slides are exposed to labeled NKEF C polypeptide. The NKEF C polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which bind to and activate and those which bind to and inhibit the receptor for the NKEF C polypeptides. As an example, a mammalian cell or membrane preparation expressing the NKEF C receptor is incubated with a labeled compound to be tested. The compound may be labeled by a variety of means known in the art, for example, by radioactivity. The ability of the compound to bind to and activate the NKEF C receptor could then be measured by the response of a known second messenger system. Such second messenger systems include, but are not limited to, CAMP guanylate cyclase, ion channels or phosphoinositide hydrolysis. For instance, an effective agonist binds to the NKEF C receptor and elicits a second messenger response while an effective antagonist binds to the receptor but does not elicit a second messenger response thereby effectively blocking the receptor.

Potential antagonists include an antibody, or in some cases, an oligopeptide, which binds to the polypeptide. Alternatively, a potential antagonist may be a closely related protein which binds to the NKEF C receptor, however, they are inactive forms of the polypeptide and thereby prevent the action of NKEF C since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of NKEF C. The antisense RNA oligonucleotide hybridizes to the mRNA in vivo and blocks translation of the mRNA molecule into NKEF C polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of NKEF C.

Potential antagonists include a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to prevent bone marrow transplant rejection. The antagonists may be employed in a composition with a pharmaceutically acceptable carrier, e.g., as hereinafter described.

The polypeptides of the present invention and agonist and antagonist compounds may be employed in combination with a suitable pharmaceutical carrier. Such compositions comprise a therapeutically effective amount of the polypeptide or agonist or antagonist compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention or agonist or antagonist compounds may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The NKEF C polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the NKEF C gene as a diagnostic. Detection of a mutated form of NKEF C will allow a diagnosis of a disease or a susceptibility to a disease which results from underexpression of NKEF C for example, tumors and viral infections.

Individuals carrying mutations in the human NKEF C gene may be detected at the DNA level by a variety of techniques. Nucleic acids for diagnosis may be obtained from a patient's cells, including, but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding NKEF C can be used to identify and analyze NKEF C mutations. For example, deletions and insertions can be detected by a change in size of the amplified product in comparison to the normal genotype. Point mutations can be identified by hybridizing amplified DNA to radiolabeled NKEF C RNA or alternatively, radiolabeled NKEF C antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of NKEF C protein in various tissues since over-expression compared to normal control tissue samples can detect the presence of a tumor or viral infection. Assays used to detect levels of NKEF C protein in a sample derived from a host are well-known to those of skill in the art and include radioiimumoassays, competitive-binding assays, Western Blot analysis and preferably an ELISA assay. An ELISA assay initially comprises preparing an antibody specific to the NKEF C antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any NKEF C proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to NKEF. Unattached reporter antibody is then washed out. Peroxidase substrates are then added to the dish and the amount of color developed in a given time period is a measurement of the amount of NKEF C protein present in a given volume of patient sample when compared against a standard curve.

A competition assay may be employed wherein antibodies specific to NKEF C are attached to a solid support and labeled NKEF C and a sample derived from the host are passed over the solid support and the amount of label detected attached to the solid support can be correlated to a quantity of NKEF C in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immmnogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Rxamples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in. the method of Graham, F. and Van der Eb, A., Virology, 52:456–457 (1973).

EXAMPLE 1

Bacterial Expression and Purification of Soluble NKEF

The DNA sequence encoding NKEF, ATCC No. 97157, is initially amplified using PCR oligonucleotide primers corresponding to the 5' sequences of the NKEF C protein and the vector sequences 3' to NKEF C. Additional nucleotides corresponding to NKEF C were added to the 5' and 3' sequences respectively. The 5' oligonucleotide primers used for the full length sequence with His-tag has the sequence 5' GCGCGGATCC ATGGAGGCGCTGCCCTGCT 3' (SEQ ID NO:3) contains a BamHI restriction enzyme site followed by NKEF C coding sequence starting from the presumed terminal amino acid of the processed protein and without the His-tag 5' CGCCCATGGAGGCGCTGC-CCCTG 3' (SEQ ID NO:4) and contains a NcoI site. The 5' primer used for the NKEF C sequence without the leader sequence and without the His-tag is 5' CGCCCATGGCTGG AGCTGTGCAGGG 3' (SEQ ID NO:5) and has a NcoI site and the 5' primer for the sequence without the leader sequence and with the His-tag is GCGCGGATCCGCTG-GAGCTGTGCAGG 3' (SEQ ID NO:7) and contains a BamHI site. The 3' primers used were as follows: 5' C G C G T C T A G A T C A A T T C A G T T T A T C-GAAATACTTCAGC 3' (SEQ ID NO:6) which contains complementary sequences to an XbaI site followed by NKEF C coding sequence; and 5' CGCGTCTAGATCAAT-TCAGTTTATCGAAATACTTCAGC 3' (SEQ ID NO:6). The restriction enzyme sites correspond to the restriction enzyme sites on the bacterial expression vector pQE-9 (Qiagen, Inc. Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with BanKI and XbaI. The amplified sequences were ligated into pQE-9 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The 0/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized NKEF C was purified from this solution by chromatography on a Nickel-Chelate column under conditions that allow for tight binding by proteins containing the 6-His tag (Hochuli, E. et al., J. Chromatography 411:177–184 (1984)). NKEF C was eluted from the column in 6 molar guanidine HCl pH 5.0 and for the purpose of renaturation adjusted to 3 molar guanidine HCl, 100 mM sodium phosphate. After incubation in this solution for 12 hours the protein was dialyzed to 10 mmolar sodium phosphate.

EXAMPLE 2

Cloning and Expression of NKEF C Using the Baculovirus Expression System

The DNA sequence encoding the full length NKEF C protein, ATCC No. 97157, was amplified using PCR oligonucleotide primers corresponding to the 5' and 3' sequences of the gene:

For the pA2-gP vector the primers have the sequence 5' CGCGGATCCCGAGGCGCTGCCCCTGC 3' (SEQ ID NO:8) and contains a BamHI restriction enzyme site (in bold) followed by an efficient signal for the initiation of translation in eukaryotic cells (Kozak, M., J. Mol. Biol., 196:947–950 (1987) and nucleotides of the NKEF C gene; and the 3' primer has the sequence 5' CGCGUTCCTCAAT-TCAGTTTATCGAAATAC 3' (SEQ ID NO:9) and contains the cleavage site for the restriction endonuclease BamHI and nucleotides complementary to the 3' non-translated sequence of the NKEF C gene.

For the pA2 vector the sequences were as follows: 5' CGC GGATCCGCCATCATGGAGGCGCTGCCCCTG 3' (SEQ ID NO:10) and contains a BamHI site and the 3' primer is 5' CGCGGATCCTCAATTCAGTTTATCGAAATCA 3' (SEQ ID NO:11) and also contains a BamHI site.

The amplified sequences were isolated from a 1% agarose gel using a commercially available kit ("Geneclean," BIO 101 Inc., La Jolla, Calif.). The fragment was then digested with the endonuclease BamHI and purified again on a 1% agarose gel. This fragment is designated F2.

The vectors pA2-GP and pA2 (modifications of pVL941 vector, discussed below) are used for the expression of the NKEF C protein using the baculovirus expression system (for review see: Summers, M. D. and Smith, G. E. 1987, A manual of methods for baculovirus vectors and insect cell culture procedures, Texas Agricultural Experimental Station Bulletin No. 1555). These expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The respective plasmid was digested with the restriction enzyme BamHI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBacNKEF) with the NKEF C gene using the enzyme BamHI. The sequence of the cloned fragment was confirmed by DNA sequencing.

5 $\mu$g of the plasmid pBacNKEF C was co-transfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid pBacNKEF C were mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 $\mu$l of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-NKEF C at a multiplicity of infection (MOI) of 2. Six hours later the medium was removed and replaced with SF900 II medium minus methionine and cysteine (Life Technologies Inc., Gaithersburg). 42 hours later 5 $\mu$Ci of $^{35}$S-methionine and 5

µCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant NKEF C in COS Cells

The expression of plasmid, NKEF C HA is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire NKEF C precursor and a HA tag fused in frame to its 3' end was cloned into the polylinker region of the vector, therefore, the recombinant protein expression is directed under the CKV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding NKEF, ATCC No. 97157, was constructed by PCR on the original EST cloned using two primers: the 5' primer 5' GCGCGGATCCACC ATGGAGGCGCTG 3' (SEQ ID NO:12) contains a BamHI site followed by 12 nucleotides of NKEF C coding sequence starting from the initiation codon; the 3' sequence 5' GCGCTCTAGATCAAGCGTAGTCTGG-GACGTCGTATGGGTAATTCAGTTTATC 3' (SEQ ID NO:13) contains complementary sequences to an XbaI site, translation stop codon, HA tag and the last 12 nucleotides of the NKEF C coding sequence (not including the stop codon). Therefore, the PCR product contains a BamHI site, NKEF C coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant NKEF, COS cells were transfected with the expression vector by DEAE-DEXTRAN method (J. Sambrook, B. Fritsch, T. Maniatis, Molecular Cloning: A Laboratory Manual, Cold Spring Laboratory Press, (1989)). The expression of the NKEF C HA protein was detected by radiolabelling and immmoprecipitation method (B. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HimdIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 5

Growth Inhibitory Activity of NKEF C Against Human Leukemia Cells

Two-fold serial dilution of purified NKEF C starting from 100 ng/ml were made in RPMI 1640 medium with 0.5% FBS. HL60 or Jurkat cells were harvested from stationary cultures and washed once with medium. Target cells were suspended at $1 \times 10^5$ cells/ml in medium containing 0.5%

FBS, then 0.1 ml aliquots were dispensed into 96-well flat-bottomed microtiter plates containing 0.1 ml serially diluted test samples. Incubation was continued for 70 hr. The activity was quantified using MTS [3(4,5-dimethyl-thiazoyl-2-yl) 5 (3-carboxymethoxyphenyl)-2-(4-sulfophenyl)-2H-tetrazolium)] Assay. MTS assay is performed by the addition of 20 µl of MTS and phenazine methosulfate (PMS) solution to 96 well plates (Stock solution was prepared as described by Promega Technical Bulletin No. 169). During a 3 hr. incubation, living cells convert the MTS into the aqueous soluble formazan product. Wells with medium only (no cells) were processed in exactly the same manner as the rest of the wells and were used for blank controls. Wells with medium and cells were used as baseline controls. The absorbence at 490 nm was recorded using an ELISA reader and is proportional to the number of viable cells in the wells. Cell growth promotion (positive percentage) or inhibition (negative percentage), as a percentage compared to baseline control wells (variation between three baseline control well is less than 5%), calculated for each sample concentration, by the formula: $OD_{experimental}/OD_{baseline\ control} \times 100-100$. All determinations were made in triplicate. Mean and SD were calculated by Microsoft Excel.

EXAMPLE 6

Antiviral Activity of NKEF C Against Vesicular Stomatitis Virus (VSV)

The cytopathic effect reduction (CPER) assay is employed to measure the protective effect of NKEF C on the infection and cytopathic process of vesicular stomatitis virus (VSV) to normal human dermal fibroblasts (NHDF) from foreskin (Clonetics). In this experiment we performed serial dilution of NKEF C at a 1:2 ratio and extended the dilution starting from 3 µg/ml to 6 ng/ml final concentration. The positive control employed in this experiment was a recombinant human IFNβ protein (expressed in *E. Coli*), which had a previously determinedspecific activity equal to $4 \times 10^6$ units per 100 µl. In addition, we maintained a negative (untreated) mock control. Semi-purified (~70%) protein isolated from *E. Coli* expressing the NKEF C protein was employed in this study. The NHDF cells were seeded at $2 \times 10^4$/well and incubated overnight to reach confluence. These cells were incubated for ~12 hours in the presence of each diluted supernatant and then subsequently challenged with VSV at an MOI equal to $1 \times 10^5$ pfu/well. The plates were further incubated for 15 hours and then fixed and stained with crystal violet. The plates were scored for CPE by estimating the percentage of cells surviving on the microtiter plate. The figure demonstrates a mean effective NKEF C concentration equal to ~100 ng/ml.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:
   (a) an amino acid sequence comprising residues +1 to +271 of SEQ ID NO:2;
   (b) an amino acid sequence comprising residues +2 to +271 of SEQ ID NO:2; and
   (c) an amino acid sequence comprising residues +31 to +271 of SEQ ID NO:2.

2. The isolated polypeptide of claim 1 which comprises amino acid sequence (a).

3. The isolated polypeptide of claim 1 which comprises amino acid sequence (b).

4. The isolated polypeptide of claim 1 which comprises amino acid sequence (c).

5. The isolated polypeptide of claim 1 wherein said amino acid sequence further comprises a heterologous polypeptide sequence.

6. A composition comprising the isolated polypeptide of claim 1 and a pharmaceutically acceptable carrier.

7. An isolated polypeptide comprising an amino acid sequence selected from the group consisting of:
   (a) an amino acid sequence of the full length polypeptide encoded by the cDNA in ATCC Deposit No. 97157;
   (b) an amino acid sequence of the full length polypeptide, excluding the N-terminal methionine residue, encoded by the cDNA in ATCC Deposit No. 97157; and
   (c) an amino acid sequence of the mature polypeptide encoded by the cDNA in ATCC Deposit No. 97157.

8. The isolated polypeptide of claim 7 which comprises amino acid sequence (a).

9. The isolated polypeptide of claim 7 which comprises amino acid sequence (b).

10. The isolated polypeptide of claim 7 which comprises amino acid sequence (c).

11. The isolated polypeptide of claim 7 wherein said amino acid sequence further comprises a heterologous polypeptide sequence.

12. A composition comprising the isolated polypeptide of claim 7 and a pharmaceutically acceptable carrier.

13. An isolated polypeptide comprising at least 30 contiguous amino acid residues of SEQ ID NO:2.

14. The isolated polypeptide of claim 13 further comprising at least 50 contiguous amino acid residues of SEQ ID NO:2.

15. The isolated polypeptide of claim 13 wherein said amino acid sequence further comprises a heterologous polypeptide sequence.

16. A composition comprising the isolated polypeptide of claim 13 and a pharmaceutically acceptable carrier.

17. The isolated polypeptide of claim 13 wherein said polypeptide has growth inhibitory activity.

18. The isolated polypeptide of claim 13 wherein said polypeptide has anti-viral activity.

19. An isolated polypeptide comprising at least 30 contiguous amino acid residues encoded by the cDNA in ATCC Deposit No. 97157.

20. The isolated polypeptide of claim 19 further comprising at least 50 contiguous amino acid residues encoded by the cDNA in ATCC Deposit No. 97157.

21. The isolated polypeptide of claim 19 wherein said amino acid sequence further comprises a heterologous polypeptide sequence.

22. A composition comprising the isolated polypeptide of claim 19 and a pharmaceutically acceptable carrier.

23. The isolated polypeptide of claim 19 wherein said polypeptide has growth inhibitory activity.

24. The isolated polypeptide of claim 19 wherein said polypeptide has anti-viral activity.

25. An isolated polypepride comprising a first amino acid sequence 95% or more identical to a second amino acid sequence selected from the group consisting of:

(a) amino acids +1 to +271 of SEQ ID NO:2;

(b) amino acids +2 to +271 of SEQ ID NO:2; and (c) amino acids +31 to +271 of SEQ ID NO:2.

26. The isolated polypeptide of claim 25 wherein said first amino acid sequence is 95% identical to said second amino acid sequence (a).

27. The isolated polypeptide of claim 25 wherein said first amino acid sequence is 95% identical to said second amino acid sequence (b).

28. The isolated polypeptide of claim 25 wherein said first amino acid sequence is 95% identical to said second amino acid sequence (c).

29. The isolated polypeptide of claim 25 wherein said amino acid sequence further comprises a heterologous polypeptide sequence.

30. A composition comprising the isolated polypeptide of claim 25 and a pharmaceutically acceptable carrier.

31. An isolated polypeptide comprising a first amino acid sequence 95% or more identical to a second amino acid sequence selected from the group consisting of:

(a) an amino acids sequence of the full length polypeptide encoded by the cDNA in ATCC Deposit No 97157;

(b) an amino acids sequence of the full length polypeptide, excluding the N-terminal methionine residue, encoded by the cDNA in ATCC Deposit No. 97157; and (c) an amino acid sequence of the manture polypeptide encoded by the cDNA in ATCC Deposit No. 97157.

32. The isolated polypeptide of claim 31 wherein said first amino acid sequence is 95% identical to said second amino acid sequence (a).

33. The isolated polypeptide of claim 31 wherein said first amino acid sequence is 95% identical to said second amino acid sequence (b).

34. The isolated polypeptide of claim 31 wherein said first amino acid sequence is 95% identical to said second amino acid sequence (c).

35. The isolated polypeptide of claim 31 wherein said amino acid sequence further comprises a heterologous polypeptide sequence.

36. A composition comprising the isolated polypeptide of claim 31 and a pharmaceutically acceptable carrier.

37. An isolated polypeptide comprising a fragment of SEQ ID NO:2, wherein said fragment has growth inhibitory activity.

38. An isolated polypeptide comprising a fragment of SEQ ID NO:2, wherein said fragment has anti-viral activity.

* * * * *

```
                        SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 31..843

(xi) SEQUENCE DESCRIPTION: SEQ ID NO:1:

AAGGGAACGT GTTTCTCCCC TCGTTTGGTC ATG GAG GCG CTG CCC CTG CTA GCC        54
                                 Met Glu Ala Leu Pro Leu Leu Ala
                                   1               5

GCG ACA ACT CCG GAC CAC GGC CGC CAC CGA AGG CTG CTT CTG CTG CCG        102
Ala Thr Thr Pro Asp His Gly Arg His Arg Arg Leu Leu Leu Leu Pro
 10              15                  20

CTA CTG CTG TTC CTG CTG CCG GCT GGA GCT GTG CAG GGC TGG GAG ACA       150
Leu Leu Leu Phe Leu Leu Pro Ala Gly Ala Val Gln Gly Trp Glu Thr
 25              30                  35              40

GAG GAG AGG CCC CGG ACT CGC GAA GAG GAG TGC CAC TTC TAC GCG GGT        198
Glu Glu Arg Pro Arg Thr Arg Glu Glu Glu Cys His Phe Tyr Ala Gly
                 45                  50                  55
```

```
GGA CAA GTG TAC CCG GGA GAG GCA TCC CGG GTA TCG GTC GCC GAC CAC        246
Gly Gln Val Tyr Pro Gly Glu Ala Ser Arg Val Ser Val Ala Asp His
            60                  65                  70

TCC CTG CAC CTA AGC AAA GCG AAG ATT TCC AAG CCA GCG CCC TAC TGG        294
Ser Leu His Leu Ser Lys Ala Lys Ile Ser Lys Pro Ala Pro Tyr Trp
        75                  80                  85

GAA GGA ACA GCT GTG ATC GAT GGA GAA TTT AAG GAG CTG AAG TTA ACT        342
Glu Gly Thr Ala Val Ile Asp Gly Glu Phe Lys Glu Leu Lys Leu Thr
    90                  95                 100

GAT TAT CGT GGG AAA TAC TTG GTT TTC TTC TTC TAC CCA CTT GAT TTC        390
Asp Tyr Arg Gly Lys Tyr Leu Val Phe Phe Phe Tyr Pro Leu Asp Phe
105                 110                 115                 120

ACA TTT GTG TGT CCA ACT GAA ATT ATC GCT TTT GGC GAC AGA CTT GAA        438
Thr Phe Val Cys Pro Thr Glu Ile Ile Ala Phe Gly Asp Arg Leu Glu
                125                 130                 135

GAA TTC AGA TCT ATA AAT ACT GAA GTG GTA GCA TGC TCT GTT GAT TCA        486
Glu Phe Arg Ser Ile Asn Thr Glu Val Val Ala Cys Ser Val Asp Ser
            140                 145                 150

CAG TTT ACC CAT TTG GCC TGG ATT AAT ACC CCT CGA AGA CAA GGA GGA        534
Gln Phe Thr His Leu Ala Trp Ile Asn Thr Pro Arg Arg Gln Gly Gly
        155                 160                 165

CTT GGG CCA ATA AGG ATT CCA CTT CTT TCA GAT TTG ACC CAT CAG ATC        582
Leu Gly Pro Ile Arg Ile Pro Leu Leu Ser Asp Leu Thr His Gln Ile
    170                 175                 180

TCA AAG GAC TAT GGT GTA TAC CTA GAG GAC TCA GGC CAC ACT CTT AGA        630
Ser Lys Asp Tyr Gly Val Tyr Leu Glu Asp Ser Gly His Thr Leu Arg
185                 190                 195                 200

GGT CTC TTC ATT ATT GAT GAC AAA GGA ATC CTA AGA CAA ATT ACT CTG        678
Gly Leu Phe Ile Ile Asp Asp Lys Gly Ile Leu Arg Gln Ile Thr Leu
                205                 210                 215

AAT GAT CTT CCT GTG GGT AGA TCA GTG GAT GAG ACA CTA CGT TTG GTT        726
Asn Asp Leu Pro Val Gly Arg Ser Val Asp Glu Thr Leu Arg Leu Val
            220                 225                 230

CAA GCA TTC CAG TAC ACT GAC AAA CAC GGA GAA GTC TGC CCT GCT GGC        774
Gln Ala Phe Gln Tyr Thr Asp Lys His Gly Glu Val Cys Pro Ala Gly
        235                 240                 245

TGG AAA CCT GGT AGT GAA ACA ATA ATC CCA GAT CCA GCT GGA AAG CTG        822
Trp Lys Pro Gly Ser Glu Thr Ile Ile Pro Asp Pro Ala Gly Lys Leu
    250                 255                 260

AAG TAT TTC GAT AAA CTG AAT TGAGAAATAC TTCTTCAAGT TATGATGCTT          873
Lys Tyr Phe Asp Lys Leu Asn
265                 270

GAAAGTTCTC AATAAAGTTC ACGGTTTCAT TACCACAAAA AAAAA                      918
```

(2) INFORMATION FOR SEQ ID NO:2:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ala Leu Pro Leu Ala Ala Thr Thr Pro Asp His Gly Arg
  1               5                  10                  15

His Arg Arg Leu Leu Leu Leu Pro Leu Leu Phe Leu Leu Pro Ala
                 20                  25                  30

Gly Ala Val Gln Gly Trp Glu Thr Glu Glu Arg Pro Arg Thr Arg Glu
             35                  40                  45
```

```
Glu Glu Cys His Phe Tyr Ala Gly Gly Gln Val Tyr Pro Gly Glu Ala
     50                  55                  60
Ser Arg Val Ser Val Ala Asp His Ser Leu His Leu Ser Lys Ala Lys
 65                  70                  75                  80
Ile Ser Lys Pro Ala Pro Tyr Trp Glu Gly Thr Ala Val Ile Asp Gly
                 85                  90                  95
Glu Phe Lys Glu Leu Lys Leu Thr Asp Tyr Arg Gly Lys Tyr Leu Val
                100                 105                 110
Phe Phe Phe Tyr Pro Leu Asp Phe Thr Phe Val Cys Pro Thr Glu Ile
                115                 120                 125
Ile Ala Phe Gly Asp Arg Leu Glu Glu Phe Arg Ser Ile Asn Thr Glu
            130                 135                 140
Val Val Ala Cys Ser Val Asp Ser Gln Phe Thr His Leu Ala Trp Ile
145                 150                 155                 160
Asn Thr Pro Arg Arg Gln Gly Gly Leu Gly Pro Ile Arg Ile Pro Leu
                    165                 170                 175
Leu Ser Asp Leu Thr His Gln Ile Ser Lys Asp Tyr Gly Val Tyr Leu
                180                 185                 190
Glu Asp Ser Gly His Thr Leu Arg Gly Leu Phe Ile Ile Asp Asp Lys
            195                 200                 205
Gly Ile Leu Arg Gln Ile Thr Leu Asn Asp Leu Pro Val Gly Arg Ser
    210                 215                 220
Val Asp Glu Thr Leu Arg Leu Val Gln Ala Phe Gln Tyr Thr Asp Lys
225                 230                 235                 240
His Gly Glu Val Cys Pro Ala Gly Trp Lys Pro Gly Ser Glu Thr Ile
                245                 250                 255
Ile Pro Asp Pro Ala Gly Lys Leu Lys Tyr Phe Asp Lys Leu Asn
                260                 265                 270

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:3:

GCGCGGATCC ATGGAGGCGC TGCCCTGCT                               29

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:4:

CGCCCATGGA GGCGCTGCCC CTG                                     23

(2) INFORMATION FOR SEQ ID NO:5:

(i) SEQUENCE CHARACTERISTICS:
        (A) LENGTH: 25 base pairs
```

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:5:

CGCCCATGGC TGGAGCTGTG CAGGG                                         25

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:6:

CGCGTCTAGA TCAATTCAGT TTATCGAAAT ACTTCAGC                            38

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:7:

GCGCGGATCC GCTGGAGCTG TGCAGG                                        26

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:8:

CGCGGATCCC GAGGCGCTGC CCCTGC                                        26

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:9:

CGCGGATCCT CAATTCAGTT TATCGAAATA C                                  31

(2) INFORMATION FOR SEQ ID NO:10:

(i) SEQUENCE CHARACTERISTICS:
```

(A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:10:

CGCGGATCCG CCATCATGGA GGCGCTGCCC CTG     33

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:11:

CGCGGATCCT CAATTCAGTT TATCGAAATC A     31

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:12:

GCGCGGATCC ACCATGGAGG CGCTG     25

(2) INFORMATION FOR SEQ ID NO:13:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:13:

GCGCTCTAGA TCAAGCGTAG TCTGGGACGT CGTATGGGTA ATTCAGTTTA TC     52

(2) INFORMATION FOR SEQ ID NO:14:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Ser Ser Gly Asn Ala Lys Ile Gly His Pro Ala Pro Asn Phe Lys
1               5                   10                  15

Ala Thr Ala Val Met Pro Asp Gly Gln Phe Lys Asp Ile Ser Leu Ser
            20                  25                  30

```
Asp Tyr Lys Gly Lys Tyr Val Val Phe Phe Tyr Pro Leu Asp Phe
         35                  40                  45

Thr Phe Val Cys Pro Thr Glu Ile Ile Ala Phe Ser Asp Arg Ala Glu
         50                  55                  60

Glu Phe Lys Lys Leu Asn Cys Gln Val Ile Gly Ala Ser Val Asp Ser
 65                  70                  75                  80

His Phe Cys His Leu Ala Trp Val Asn Thr Pro Lys Lys Gln Gly Gly
             85                  90                  95

Leu Gly Pro Met Asn Ile Pro Leu Val Ser Asp Pro Lys Arg Thr Ile
                100                 105                 110

Ala Gln Asp Tyr Gly Val Leu Lys Ala Asp Glu Gly Ile Ser Phe Arg
            115                 120                 125

Gly Leu Phe Ile Ile Asp Asp Lys Gly Ile Leu Arg Gln Ile Thr Val
            130                 135                 140

Asn Asp Pro Pro Cys Cys Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Pro Lys Thr Lys
                180                 185                 190

Glu Tyr Phe Ser Lys Gln Lys
            195

(2) INFORMATION FOR SEQ ID NO:15:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

Met Ala Ser Gly Asn Ala Arg Ile Gly Lys Pro Ala Pro Asp Phe Lys
 1               5                  10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
            35                  40                  45

Phe Val Cys Pro Thr Glu Ile Ile Ala Phe Ser Asn Arg Ala Glu Asp
         50                  55                  60

Phe Arg Lys Leu Gly Cys Glu Val Leu Gly Val Ser Val Asp Ser Gln
 65                  70                  75                  80

Phe Asn His Leu Ala Trp Ile Asn Thr Pro Arg Lys Glu Gly Gly Leu
             85                  90                  95

Gly Pro Leu Asn Ile Pro Leu Leu Gly Asp Val Thr Arg Arg Leu Ser
                100                 105                 110

Glu Asp Tyr Gly Val Leu Lys Thr Asp Glu Gly Ile Ala Tyr Arg Gly
            115                 120                 125

Leu Phe Ile Ile Asp Gly Lys Gly Val Leu Arg Gln Ile Thr Val Asn
            130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175
```

```
Lys Pro Gly Ser Asp Thr Ile Lys Pro Asn Val Asp Asp Ser Lys Glu
                180                 185                 190

Tyr Phe Ser Lys His Asn
        195
```

(2) INFORMATION FOR SEQ ID NO:16:

(i) SEQUENCE CHARACTERISTICS:
        (A) LENGTH: 257 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Met Ala Ala Ala Gly Arg Leu Leu Trp Ser Ser Val Ala Arg Gly
1               5                   10                  15

Ala Ser Ala Ile Ser Arg Ser Ile Ser Ala Ser Thr Val Leu Arg Pro
                20                  25                  30

Val Ala Ser Arg Arg Thr Cys Leu Thr Asp Ile Leu Trp Ser Ala Ser
            35                  40                  45

Ala Gln Gly Lys Ser Ala Phe Ser Thr Ser Ser Phe His Thr Pro
50                  55                  60

Ala Val Thr Gln His Ala Pro Tyr Phe Lys Gly Thr Ala Val Val Asn
65                  70                  75                  80

Gly Glu Phe Lys Glu Leu Ser Leu Asp Asp Phe Lys Gly Lys Tyr Leu
                85                  90                  95

Val Leu Phe Phe Tyr Pro Leu Asp Phe Thr Phe Val Cys Pro Thr Glu
                100                 105                 110

Ile Val Ala Phe Ser Asp Lys Ala Asn Glu Phe His Asp Val Asn Cys
            115                 120                 125

Glu Val Val Ala Val Ser Val Asp Ser His Phe Ser His Leu Ala Trp
130                 135                 140

Ile Asn Thr Pro Arg Lys Asn Gly Gly Leu Gly His Met Asn Ile Thr
145                 150                 155                 160

Leu Leu Ser Asp Ile Thr Lys Gln Ile Ser Arg Asp Tyr Gly Val Leu
                165                 170                 175

Leu Glu Ser Ala Gly Ile Ala Leu Arg Gly Leu Phe Ile Ile Asp Pro
                180                 185                 190

Asn Gly Val Val Lys His Leu Ser Val Asn Asp Leu Pro Val Gly Arg
            195                 200                 205

Ser Val Glu Glu Thr Leu Arg Leu Val Lys Ala Phe Gln Phe Val Glu
            210                 215                 220

Thr His Gly Glu Val Cys Pro Ala Asn Trp Thr Pro Glu Ser Pro Thr
225                 230                 235                 240

Ile Lys Pro Ser Pro Thr Ala Ser Lys Glu Tyr Phe Glu Lys Val His
                245                 250                 255

Gln
```

(2) INFORMATION FOR SEQ ID NO:17:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Met Ser Ser Gly Asn Ala Lys Ile Gly Tyr Pro Ala Pro Asn Phe Lys
1               5                   10                  15

Ala Thr Ala Val Met Pro Asp Gly Gln Phe Lys Asp Ile Ser Leu Ser
                20                  25                  30

Glu Tyr Lys Gly Lys Tyr Val Val Phe Phe Phe Tyr Pro Leu Asp Phe
            35              40                  45

Thr Phe Val Cys Pro Thr Glu Ile Ile Ala Phe Ser Asp Arg Ala Asp
        50              55                  60

Glu Phe Lys Lys Leu Asn Cys Gln Val Ile Gly Ala Ser Val Asp Ser
65                  70                  75                  80

His Phe Cys His Leu Ala Trp Ile Asn Thr Pro Lys Lys Gln Gly Gly
                85                  90                  95

Leu Gly Pro Met Asn Ile Pro Leu Ile Ser Asp Pro Lys Arg Thr Ile
                100                 105                 110

Ala Gln Asp Tyr Gly Val Leu Lys Ala Asp Glu Gly Ile Ser Phe Arg
            115                 120                 125

Gly Leu Phe Ile Ile Asp Asp Lys Gly Ile Leu Arg Gln Ile Thr Ile
            130                 135                 140

Asn Asp Leu Pro Val Gly Arg Ser Val Asp Glu Ile Ile Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Asn Lys Ser Lys
                180                 185                 190

Glu Tyr Phe Ser Lys Gln Lys
                195
```